(12) United States Patent
Sukopp et al.

(10) Patent No.: US 8,263,783 B2
(45) Date of Patent: *Sep. 11, 2012

(54) PROCESS FOR THE SULFINYLATION OF A PYRAZOLE DERIVATIVE

(75) Inventors: Martin Sukopp, Mannheim (DE); Oliver Kuhn, Rosport (LU); Carsten Gröning, Mannheim (DE); Michael Keil, Freinsheim (DE); Jon J. Longlet, Nederland, TX (US)

(73) Assignee: BASF SE, Ludwigshafen (DE)

( * ) Notice: Subject to any disclaimer, the term of this patent is extended or adjusted under 35 U.S.C. 154(b) by 210 days.

This patent is subject to a terminal disclaimer.

(21) Appl. No.: 12/514,098

(22) PCT Filed: Nov. 5, 2007

(86) PCT No.: PCT/EP2007/061891
§ 371 (c)(1),
(2), (4) Date: May 8, 2009

(87) PCT Pub. No.: WO2008/055877
PCT Pub. Date: May 15, 2008

(65) Prior Publication Data
US 2010/0137395 A1    Jun. 3, 2010

Related U.S. Application Data

(60) Provisional application No. 60/865,178, filed on Nov. 10, 2006, provisional application No. 60/913,617, filed on Apr. 24, 2007.

(51) Int. Cl.
*C07D 231/18* (2006.01)
(52) U.S. Cl. .................................................. 548/367.4
(58) Field of Classification Search .................. None
See application file for complete search history.

(56) References Cited

U.S. PATENT DOCUMENTS

| 4,724,095 | A | 2/1988 | Gresser |
| 5,618,945 | A * | 4/1997 | Casado et al. ............. 548/367.4 |
| 6,203,670 | B1 | 3/2001 | Forat et al. |
| 6,399,815 | B2 | 6/2002 | Suzuki |
| 2011/0190510 | A1 | 8/2011 | Sukopp et al. |

FOREIGN PATENT DOCUMENTS

| CN | 1 374 298 | 10/2002 |
| DE | 198 53 560 | 5/2000 |
| EP | 0 165 136 | 12/1985 |
| EP | 0 295 117 | 12/1988 |
| EP | 0 668 269 | 8/1995 |
| EP | 1 331 222 | 7/2003 |
| WO | WO 99/32439 | 7/1999 |
| WO | WO 01/30760 | 5/2001 |
| WO | WO 2008/055879 | 5/2008 |
| WO | WO 2008/055880 | 5/2008 |
| WO | WO 2009/068533 | 6/2009 |
| WO | WO 2010/037693 | 9/2009 |

OTHER PUBLICATIONS

International Search Report completed Mar. 19, 2008, in International Application No. PCT/EP2007/061891, filed Nov. 5, 2007.
International Preliminary Report on Patentability dated Feb. 20, 2008, from corresponding International Application No. PCT/EP2007/061891, filed Nov. 5, 2007.
Billard, Thierry, et al., "A New Equivalent of the CF3S(O)+ Cation. Synthesis of Trifluoromethanesulfinates andTrifluoromethanesulfinamides", Tetrahedron, 1999, p. 7243-7250, vol. 55.
Huilong, Yang et al., "Study on the Synthesis of Regent", Journal of Hebei University of Science and Technology, 2004, p. 69-73, vol. 25, No. 2, Translation provided.
Ren, Qing-Yun, et al., "Research Progress on Synthesis of Fipronil and its Main Intermediate", Chinese Journal of Pesticides, 2004, pp. 529-531, vol. 43, No. 12.
Wakselman, Claude, et al., "Aryltrifluoromethylsulfoxides: Sulfinylation of Aromatics by Triflinate Salts in Acid Medium", Synlett, 2001, p. 550-552, No. 4.
Roesky, H.W. et al., "Perfluoroalkansulfinsaeure-ester, -amide und isocyanate", Chem.Ber. 1974, p. 508-517, vol. 107, English translation provided.
Andrieux, C.P. et al., "Outer-Sphere and Inner-Sphere Processes in Organic Chemistry. Reaction of Trifluoromethyl Bromide with Electrochemically Generated Aromatic Anion Radicals and Sulfer Dioxide Anion Radicals", J. Am. Chem. Soc. 112, (1990), pp. 786-791.
Harzdorf, C. et al., "On perfluoroalkanesulfinic acids", Liebigs Ann. Chem., 1973, pp. 33-39, Translation Provided.

* cited by examiner

*Primary Examiner* — Joseph K. McKane
*Assistant Examiner* — Alicia L Otton
(74) *Attorney, Agent, or Firm* — Brinks Hofer Gilson & Lione

(57) ABSTRACT

The present invention relates to a process for the sulfinylation of a pyrazole derivative, characterized in that 5-amino-1-[2,6-dichloro-4-(trifluoromethyl)phenyl]-1H-pyrazole-3-carbonitrile (II) is reacted with a sulfinylating agent selected from trifluoromethylsulfinic acid, trifluoromethylsulfinic acid anhydride, and a trifluoromethylsulfinate alkaline or alkaline earth metal salt and mixtures of the acid and/or the salt(s), in the presence of at least one amine acid complex wherein the amine(s) are selected from tertiary amines and the acid(s) are selected from hydrofluoric, hydrochloric, hydrobromic and hydroiodic acid and sulfonic acid derivatives, and with the addition of a halogenating agent.

18 Claims, No Drawings

PROCESS FOR THE SULFINYLATION OF A PYRAZOLE DERIVATIVE

This application is a National Stage application of International Application No. PCT/EP2007/061891 filed Nov. 5, 2007, which claims the benefit of U.S. Provisional Application Nos. 60/865,178 and 60/913,617, filed Nov. 10, 2006 and Apr. 24, 2007, respectively; the entire contents of all aforementioned applications are hereby incorporated herein by reference.

The present invention relates to a novel process for the sulfinylation of a pyrazole derivative, characterized in that 5-amino-1-[2,6-dichloro-4-(trifluoromethyl)phenyl]-1H-pyrazole-3-carbonitrile (II) is reacted with a sulfinylating agent selected from trifluoromethylsulfinic acid, trifluoromethylsulfinic acid anhydride, and a trifluoromethylsulfinate alkaline or alkaline earth metal salt and mixtures of the acid and/or the salt(s), in the presence of at least one amine acid complex wherein the amine(s) are selected from tertiary amines and the acid(s) are selected from hydrofluoric, hydrochloric, hydrobromic and hydroiodic acid and sulfonic acid derivatives, and with the addition of a halogenating agent.

The sulfinylation of a pyrazole-type compound refers to the substitution of a hydrogen atom on a pyrazole heterocycle carbon atom by an RS(=O)— group.

The direct sulfinylation of various organic molecules (not including pyrazole derivatives) employing a mixture of P(O)Cl$_3$ and CF$_3$S(O)ONa has been described in T. Billard, A. Greiner, B. R. Langlois, Tetrahedron 55 (1999), p. 7243-7250. Likewise, C. Wakselman, M. Tordeux, C. Freslon, L. Saint-Jalmes, Synlett 2001, p. 550-552 teaches that direct sulfinylation of aromatic compounds takes place by CF$_3$S(O)ONa or CF$_3$S(O)OK in the presence of triflic acid (CF$_3$S(O)$_2$OH).

Processes for the direct sulfinylation of 5-amino-1-[2,6-dichloro-4-(trifluoromethyl)phenyl]-1H-pyrazole-3-carbonitrile (II) have been described in EP-A 668 269, EP-A 1 331 222, CN-A 1374298, and in Y. Huilong, M. Zengeng, W. Shujuan, J. Hebei University of Science of Technology, Vol. 25(2), Sum 69 (2004), Serial no. 1008-1542 (2004) 02-0018-03.

In EP 668 269, the sulfinylation of 5-amino-1-[2,6-dichloro-4-(trifluoromethyl)phenyl]-1H-pyrazole-3-carbonitrile (II) with trifluoromethylsulfinic acid CF$_3$S(O)OH and its derivatives CF$_3$S(O)Cl, CF$_3$S(O)ONa, CF$_3$S(O)N(CH$_3$)$_2$, or CF$_3$S(O)N(CH$_2$CH$_3$)$_2$ has been described. As chlorinating agent, phosgene, chloroformates, PCl$_5$ and SOCl$_2$ are mentioned. It is described that a reagent ("compound C") chosen from the group consisting of the tosylates, hydrochlorides and mesylates of a primary, secondary, or tertiary amine, preferably of dimethylamine, of pyridine, of trimethylamine, of diethylamine or of isopropylamine or gaseous hydrogen chloride, optionally in the presence of an equimolar amount of para-toluenesulfonic acid, may be added to complete the reaction. Examples are given for the following combinations of reactants:

CF$_3$S(O)Cl, dimethylamine p-tosylate;
CF$_3$S(O)Cl, pyridine hydrochloride salt;
CF$_3$S(O)N(CH$_3$)$_2$, p-toluolsulfonic acid, hydrochloric acid;
CF$_3$S(O)Cl, dimethylamine p-tosylate, hydrochloric acid; and
CF$_3$S(O)ONa, dimethylamine p-tosylate, SOCl$_2$.

The reactions carried out with CF$_3$S(O)Cl as the sulfinylating agent give the highest yield of the final product.

The process described in CN-A 1374298 has been developed to overcome certain shortcomings of the process described in EP 668 269. CN-A 1374298 cites that CF$_3$S(O)Cl is extremely unstable, CF$_3$S(O)N(CH$_3$)$_2$ and CF$_3$SOOH are relatively difficult to prepare, that the reactivity CF$_3$S(O)ONa is not high, and that the yield in the sulfinylation reaction is correspondingly relatively low. CN-A 1374298 describes the sulfinylation of 5-amino-1-[2,6-dichloro-4-(trifluoromethyl)phenyl]-1H-pyrazole-3-carbonitrile (II) with the potassium salt of trifluoromethylsulfinic acid, CF$_3$S(O)OK, or mixtures of the potassium and the sodium salt of trifluoromethylsulfinic acid, CF$_3$S(O)OK with CF$_3$S(O)ONa, wherein the sulfinylating agent is combined with POCl$_3$, PCl$_3$, SOCl$_2$, COCl$_2$, or trichloromethylchloromethanoate. Optionally, the amine acid complex dimethylamine p-tosylate can be added to complete the reaction.

Examples are given for the following combinations of reactants:

CF$_3$S(O)OK; dimethylamine p-tosylate; POCl$_3$; and
CF$_3$S(O)OK/Na; dimethylamine p-tosylate; SOCl$_2$.

Huilong et al. describes the reaction of 5-amino-1-[2,6-dichloro-4-(trifluoromethyl)phenyl]-1H-pyrazole-3-carbonitrile (II) with the sodium salt of trifluoromethylsulfinic acid (CF$_3$S(O)ONa), dimethylamine p-tosylate, and SOCl$_2$, with addition of catalytic amounts of DMF (dimethylformamide).

In EP-A 1 331 222, 5-amino-1-[2,6-dichloro-4-(trifluoromethyl)phenyl]-1H-pyrazole-3-carbonitrile (II) is sulfinylated using N-trifluoromethylsulfinylsuccinimide as the sulfinylating agent in the presence of triethylamine and without the addition of a chlorinating agent. The intermediate N-trifluoromethylsulfinylamino-pyrazole is isolated and under the conditions of a Thia-Fries rearrangement transformed into the final product 5-amino-1-[2,6-dichloro-4-(trifluoromethyl)phenyl]-4-(trifluoromethylsulfinyl)-pyrazole-3-carbonitrile.

Thus, the sulfinylation of 5-amino-1-[2,6-dichloro-4-(trifluoromethyl)phenyl]-1H-pyrazole-3-carbonitrile (II) to the final product 5-amino-1-[2,6-dichloro-4-(trifluoromethyl)phenyl]-4-(trifluoromethylsulfinyl)-pyrazole-3-carbonitrile (common name: fipronil) has received considerable attention in the literature, the focus being on the optimization of the sulfinylating agent.

However, and also as cited in the recent review article "research progress on synthesis of fipronil and its main intermediates", Chinese Journal of Pesticides, 2004, Vol. 43, no. 12, 529-531, the sulfinylation of the pyrazole intermediate was still found not to be generally suitable for a large scale industrial production.

The reaction product of the present sulfinylation is fipronil, which is a market insecticide of considerable importance. Generally, technical manufacturing processes of pesticides have to fulfill high requirements with regard to yield and purity of the product, for reasons of profitability, but also, most important, in order to avoid the presence of potentially noxious side products. This is of special relevance for fipronil as it is also used in animal health products and therefore also comes into contact with companion animals.

It is also a legal requirement for technical manufacturing processes to avoid exposure of the plant employees but also of the environment to reagents which can have adverse effects to the health of the employees or environment. Therefore, it is desirable to have a technical manufacturing process at hand which avoids the use of toxic reagents such as CF$_3$S(O)Cl.

Furthermore, during the scale up of a process from the laboratory scale to a technical scale, problems may arise that were not as such or to the respective extend foreseeable in the laboratory.

For example, the filling and/or dissolution of voluminous starting materials may take much longer on a big scale than in a small vessel, with the effect that the kinetic of the reaction is significantly changed, and thereby the conversion and the product spectrum.

Another example that can be mentioned is the appearance of side products that are, due to solubility or texture, difficult to separate from the desired main product on a large scale. Problems with extraction, filtration and clogging of filters may occur. Insoluble starting materials or reaction (side) products may also challenge the agitation, heat dissipation or pumping thus leading to inhomogenous reaction mixtures.

Yet another challenge is the control of the course of the reaction temperature in large-scale processes. The temperature rates generally are lower which may have an influence on the side product spectrum. As high reaction temperatures and/or aggressive reaction media may cause corrosion, and also because of economic reasons, moderate reaction conditions (low temperatures) are preferred.

Hygroscopic properties of solids can complicate reactions that favorably are conducted under essentially water free conditions. For example, when the process as defined above is conducted using an amine acid complex wherein the acid is $H_2SO_4$— and not an acid as defined for the inventive process—the yield of the reaction is extremely poor.

Nonreactive catalysts—such as tertiary amines, e.g. triethylamine acids—are preferably used in the inventive process in order to avoid side reactions. Secondary or primary amines can react with the sulfinylating agent.

With a view to facilitating the work-up, reagents are preferably used that can be removed by distillation. Solids are removed by washing with acidic or alkaline solvents. It is not advantageous to employ reagents that have phase transfer catalytic properties which may hinder a phase separation during work-up.

Against this background and facing the fact that one of the essential starting materials for the current industrial production of fipronil is $CF_3Br$ (see e.g. WO 01/30760) which exhibits high environmental toxicity and is scheduled for production phase out by the Montreal Protocol on Substances that Deplete the Ozone Layer (it may then be used only as a feedstock material), it was an object of the present invention to develop a new, large scale industrial process for the manufacturing of fipronil which gives fipronil in high purity and yield while avoiding the use of dangerous reagents and avoiding problems with the technical reaction control.

Accordingly, the process defined at the outset was found. The obtained product fipronil is suitable for use as a pesticide for agricultural uses as well as non-crop uses for combating pests. Also, the obtained fipronil is suitable for use in the animal health field for combating animal health pests and parasites, especially for the long lasting protection against fleas and ticks on mammals.

Thus, the current invention also pertains to pesticidal or parasiticidal composition containing 5-amino-1-[2,6-dichloro-4-(trifluoromethyl)phenyl]-4-(trifluoromethylsulfinyl)-pyrazole-3-carbonitrile as prepared by the inventive process.

Likewise, the present invention relates to a method for the control of insects, acarids or nematodes by contacting the insect, acarid or nematode or their food supply, habitat, breeding ground or their locus with a pesticidally effective amount of 5-amino-1-[2,6-dichloro-4-(trifluoromethyl)phenyl]-4-(trifluoromethylsulfinyl)-pyrazole-3-carbonitrile prepared by the inventive process as well as to a method of protecting growing plants from attack or infestation by insects, acarids or nematodes by applying to the foliage or the seeds of the plants, or to the soil or water in which they are growing, a pesticidally effective amount of 5-amino-1-[2,6-dichloro-4-(trifluoromethyl)phenyl]-4-(trifluoromethylsulfinyl)-pyrazole-3-carbonitrile prepared by the inventive process. According to these methods, 5-amino-1-[2,6-dichloro-4-(trifluoromethyl)phenyl]-4-(trifluoromethylsulfinyl)-pyrazole-3-carbonitrile is usually applied in an amount of from 5 g/ha to 2000 g/ha.

Moreover, the present invention relates to a method for treating, controlling, preventing or protecting animals against infestation or infection by parasites which comprises orally, topically or parenterally administering or applying to the animals or their habitat a parasiticidally effective amount of 5-amino-1-[2,6-dichloro-4-(trifluoromethyl)phenyl]-4-(trifluoromethylsulfinyl)-pyrazole-3-carbonitrile prepared by the inventive process or its veterinarily acceptable enantiomers or salts.

Also, the present invention relates to a process for the preparation of a composition for treating, controlling, preventing or protecting animals against infestation or infection by parasites which comprises admixing 5-amino-1-[2,6-dichloro-4-(trifluoromethyl)phenyl]-4-(trifluoromethylsulfinyl)-pyrazole-3-carbonitrile prepared by the inventive process or its enantiomers or veterinarily acceptable salts with a veterinarily acceptable carrier. The composition may either be a concentrate or contains 5-amino-1-[2,6-dichloro-4-(trifluoromethyl)phenyl]-4-(trifluoromethylsulfinyl)-pyrazole-3-carbonitrile in a parasiticidally effective amount.

While there are examples given for certain amine acid complexes added at the beginning or during the course of the sulfinylation reaction, there is no teaching as to the crucial importance of the specific nature of the amine acid complex with regard to reaction control or to the yield and/or the purity of the final product fipronil.

In none of the prior art documents, mention is made of the favorable combination of the key features of the present invention, namely employing
a) trifluoromethylsulfinic acid, trifluoromethylsulfinic acid anhydride, or a trifluoromethylsulfinate alkaline or alkaline earth metal salt, or mixtures of the acid and/or the salt(s) as sulfinylating agents and
b) at least one amine acid complex wherein the amine(s) are selected from tertiary amines and the acid(s) are selected from hydrofluoric, hydrochloric, hydrobromic and hydroiodic acid and sulfonic acid derivatives.

In EP-A1 668 269, the sulfinylating agents $CF_3S(O)Cl$, $CF_3S(O)N(CH_3)_2$, $CF_3S(O)N(CH_2CH_3)_2$, $CF_3S(O)OH$ and $CF_3S(O)ONa$, together with phosgene or $SOCl_2$ or $ClCO_2C_2H_5$ are described as being equivalent alternatives in processes leading to fipronil and its close analgon 5-amino-1-[2,6-dichloro-4-(pentafluorosulfanyl)phenyl]-4-(trifluoromethylsulfinyl)-pyrazole-3-carbonitrile. One example is given for the use of $CF_3S(O)ONa$, but not together with tertiary amines as part of the amine acid complex.

Also, in EP-A1 668 269, the following list of preferred amines is given: tosylates, hydrochlorides or mesylates of dimethylamine, pyridine, trimethylamine, diethylamine, isopropylamine. An example is given for pyridine hydrochloride as amine acid complex, however used together with $CF_3S(O)Cl$ as the sulfinylating agent.

The novel subject of the present invention thus is the sulfinylation of 5-amino-1-[2,6-dichloro-4-(trifluoromethyl)phenyl]-1H-pyrazole-3-carbonitrile (II) with a sulfinylating agent selected from trifluoromethylsulfinic acid, trifluoromethylsulfinic acid anhydride and a trifluoromethylsulfinate alkaline or alkaline earth metal salt and mixtures of the acid and/or the salt(s), in the presence of at least one amine acid complex wherein the amine(s) are selected from tertiary amines and the acid(s) are selected from hydrofluoric, hydrochloric, hydrobromic and hydroiodic acid and sulfonic acid derivatives, and with the addition of a halogenating agent.

A reaction scheme may be depicted as follows:

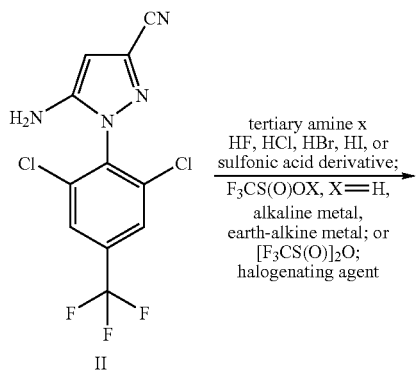

tertiary amine x
HF, HCl, HBr, HI, or
sulfonic acid derivative;
$F_3CS(O)OX$, X═H,
alkaline metal,
earth-alkine metal; or
$[F_3CS(O)]_2O$;
halogenating agent

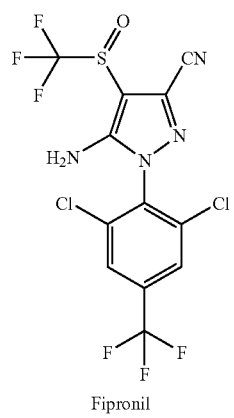

Fipronil

The sulfinylating agent is preferably selected from trifluoromethylsulfinic acid, trifluoromethylsulfinic acid anhydride, trifluoromethylsulfinate sodium salt, trifluoromethylsulfinate potassium salt, and mixtures of these.

According to a preferred embodiment of the present invention, trifluoromethylsulfinate sodium salt is used as the sulfinylating agent.

According to another preferred embodiment of the present invention, trifluoromethylsulfinate potassium salt is used as the sulfinylating agent.

According to yet another preferred embodiment of the present invention, trifluoromethylsulfinic acid is used as the sulfinylating agent.

According to yet another preferred embodiment of the present invention, trifluoromethylsulfinic acid anhydride is used as the sulfinylating agent.

According to a preferred embodiment of the present invention, a mixture of the trifluoromethylsulfinate sodium and potassium salts, in a mixing ratio of from 0.01:99.99 weight % to 50:50 weight % is used as the sulfinylating agent.

Preferably, 1.0 to 1.35 molar equivalents, most preferably 1.2 molar equivalents, of the sulfinylating agent relative to 5-amino-1-[2,6-dichloro-4-(trifluoromethyl)phenyl]-1H-pyrazole-3-carbonitrile are used.

In a preferred embodiment, the sulfinylating agent is dried before its use until it is essentially water-free. "Water free" means that the content of water in the solid does not exceed 5 ppm to 100 ppm.

The halogenating agent is selected from thionylchloride, thionylbromide, phosphoroxychloride, oxalylchloride, phosgen, triphosgen $((CCl_3)_2C(═O))$, chloroformiates, phosphorpentachloride, phosphortrichloride, trichloromethylchloromethanoat, and xylenesulfonic acid chloride.

According to a preferred embodiment of the present invention, a chlorinating agent is used as the halogenating agent. Preferably, thionylchloride or phosphoroxychloride are used as the chlorinating agent.

According to another preferred embodiment of the present invention, phosphoroxychloride is used as the chlorinating agent.

Most preferably, thionylchloride is used as the chlorinating agent.

Preferably, 1.15 to 1.35 molar equivalents, most preferably about 1.2 molar equivalents, of the halogenating agent relative to 5-amino-1-[2,6-dichloro-4-(trifluoromethyl)phenyl]-1H-pyrazole-3-carbonitrile are used.

We have found that the choice of the amine acid complex plays a key role in the sulfinylation of 5-amino-1-[2,6-dichloro-4-(trifluoromethyl)phenyl]-1H-pyrazole-3-carbonitrile. Critical properties that influence the sulfinylating reaction are steric (bulk) properties and molecular weight, and also pKs value and solubility.

The sulfinylation reaction of the present invention is a one-pot synthesis of a two-step reaction. The first step involves the addition of the CF3S(O)— group to the amino group of the pyrazole ring. In a second step, fipronil is formed via a Thia-Fries rearrangement:

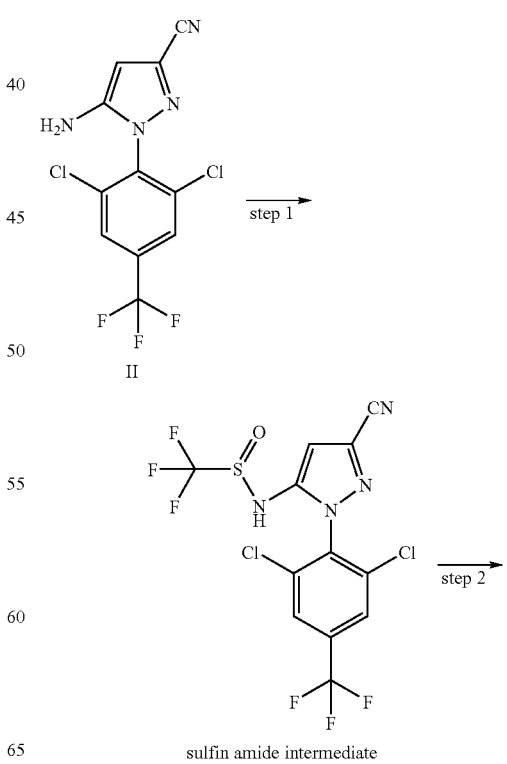

sulfin amide intermediate

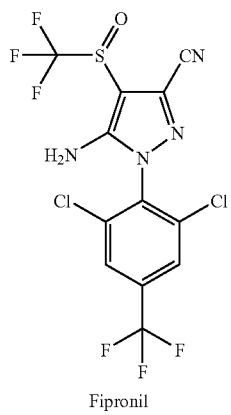

Fipronil

The amine acid complex has two functions in this two-step reaction: (1) when sulfinylates are used as sulfinylating agents, it catalyzes the activation of the sulfinylate with the halogenating agent via intermediate formation of sulfinic acid. For this, catalytical amounts of 0.01 to 1.0 molar equivalents of amine acid complex relative to the pyrazole compound II are needed. (2) It accelerates the Thia-Fries rearrangement and has a significant influence on selectivity. With a view to obtain high yields and high purity, overall amounts of above 1 molar equivalents of amine acid complex relative to the pyrazole compound II are advantageously used for step two.

Preferred are amine acid complexes exhibiting low or essentially no hygroscopicity, as the sulfinylating process of the present invention advantageously is conducted in the essential absence of water (i.e. below 5 to 100 ppm of water).

Preferred tertiary amines are alkyl amines such as trimethylamine, triethylamine, tripropylamine, triisopropylamine, tributylamine, dimethyl ethyl amine, diethyl methylamine, dimethyl n-propyl amine, diisopropyl ethyl amine, DBU (1,8-diazabicyclo[5.4.0]undec-7-ene), DBN (1,5-diazabicyclo[4.3.0]non-5-ene), methyl morpholine, ethyl morpholine, N,N-dimethylaniline, methyl piperidine, methylpyrrolidine, or methyldibenzylamine; or aromatic amines such as pyridine, DMAP (dimethylaminopyridine), collidine, lutidine, pyrimidine, pyrazine, or piperazine.

In a further preferred embodiment, the tertiary amine is selected from triethylamine, tripropylamine, triisopropylamine, dimethyl ethyl amine, diethyl methylamine, dimethyl n-propyl amine, diisopropylethylamine, DBU (1,8-diazabicyclo[5.4.0]undec-7-ene), DBN (1,5-diazabicyclo[4.3.0]non-5-ene), methyl morpholine, ethyl morpholine, N,N-dimethylaniline, methyl piperidine, methylpyrrolidine, and methyldibenzylamine, DMAP (dimethylaminopyridine), collidine, lutidine, pyrimidine, pyrazine, and piperazine.

In another preferred embodiment, the tertiary amine is selected from trimethylamine, triethylamine, dimethyl ethyl amine, diethyl methylamine, dimethyl n-propyl amine, methyl morpholine, N,N-dimethylaniline, methyl piperidine, methylpyrrolidine, methyldibenzylamine, and pyridine.

Especially preferred are trimethylamine, triethylamine, dimethyl ethyl amine, dimethyl n-propyl amine, or pyridine. Very preferred are triethylamine and pyridine. In a very preferred embodiment, the amine is triethylamine. Also, in a very preferred embodiment the amine is pyridine. Also, in a very preferred embodiment the amine is trimethylamine. Also, in a very preferred embodiment at least one of the alkyl groups attached to the nitrogen atom of the amine is a methyl group.

Also, in a very preferred embodiment the nitrogen atom of the amine group is sp3 hybridized, i.e. it does not form a double bond to a neighbour atom.

Preferred acids of the amine acid complex for use in the present invention are hydrochloric acid, hydrofluoric acid, hydrobromic acid, hydroiodic acid or sulfonic acid derivatives such as aromatic sulfonic acids, e.g. p-toluenesulfonic acid, benzenesulfonic acid, 4-ethyl benzenesulfonic acid, 4-chlorobenzenesulfonic acid, xylene sulfonic acid, 2,3-dimethylbenzene sulfonic acid, 2,4-dimethylbenzene sulfonic acid, 2,5-dimethylbenzene sulfonic acid, 2,6-dimethylbenzene sulfonic acid, 1-napthalenesulfonic acid, 2-napthalenesulfonic acid, mixtures of two or more of the isomers of dimethylbenzene sulfonic acids, or mesitylene sulfonic acid; or alkyl sulfonic acids, e.g. methane sulfonic acid or camphor sulfonic acid; or haloalkylsulfonic acids, e.g. trifluoromethylsulfonic acid.

More preferred acids of the amine acid complex for use in the present invention are hydrochloric acid, hydrofluoric acid, or sulfonic acid derivatives such as aromatic sulfonic acids, e.g. p-toluenesulfonic acid, benzenesulfonic acid, xylene sulfonic acid, mesitylene sulfonic acid; or alkyl sulfonic acids, e.g. methanesulfonic acid; or haloalkylsulfonic acids, e.g. trifluoromethylsulfonic acid.

Especially preferred are acids with a pKs-value of below 2.

From the choice of amine acid complexes as used in the present invention, those with a pKa below 6, preferably 5, and above 10 are preferred.

Most preferred acids are hydrochloric acid, p-toluenesulfonic acid, xylene sulfonic acid, or benzene sulfonic acid.

The most preferred acid with regard to optimized yield is hydrochloride acid.

Preferred amine acid complexes Q are listed in Table 1 which follows.

TABLE 1

| No. | amine | Acid |
|---|---|---|
| Q-1 | N(CH$_3$)$_3$ | HF |
| Q-2 | N(CH$_3$)$_3$ | HCl |
| Q-3 | N(CH$_3$)$_3$ | HBr |
| Q-4 | N(CH$_3$)$_3$ | HI |
| Q-5 | N(CH$_3$)$_3$ | p-toluene sulfonic acid |
| Q-6 | N(CH$_3$)$_3$ | benzene sulfonic acid |
| Q-7 | N(CH$_3$)$_3$ | xylene sulfonic acid |
| Q-8 | N(CH$_3$)$_3$ | methane sulfonic acid |
| Q-9 | N(CH$_3$)$_3$ | trifluoromethyl sulfonic acid |
| Q-10 | N(CH$_3$)$_3$ | mesitylene sulfonic acid |
| Q-11 | N(CH$_2$CH$_3$)$_3$ | HF |
| Q-12 | N(CH$_2$CH$_3$)$_3$ | HCl |
| Q-13 | N(CH$_2$CH$_3$)$_3$ | HBr |
| Q-14 | N(CH$_2$CH$_3$)$_3$ | HI |
| Q-15 | N(CH$_2$CH$_3$)$_3$ | p-toluene sulfonic acid |
| Q-16 | N(CH$_2$CH$_3$)$_3$ | benzene sulfonic acid |
| Q-17 | N(CH$_2$CH$_3$)$_3$ | xylene sulfonic acid |
| Q-18 | N(CH$_2$CH$_3$)$_3$ | methane sulfonic acid |
| Q-19 | N(CH$_2$CH$_3$)$_3$ | trifluoromethyl sulfonic acid |
| Q-20 | N(CH$_2$CH$_3$)$_3$ | mesitylene sulfonic acid |
| Q-21 | N(CH$_2$CH$_2$CH$_3$)$_3$ | HF |
| Q-22 | N(CH$_2$CH$_2$CH$_3$)$_3$ | HCl |
| Q-23 | N(CH$_2$CH$_2$CH$_3$)$_3$ | HBr |
| Q-24 | N(CH$_2$CH$_2$CH$_3$)$_3$ | HI |
| Q-25 | N(CH$_2$CH$_2$CH$_3$)$_3$ | p-toluene sulfonic acid |
| Q-26 | N(CH$_2$CH$_2$CH$_3$)$_3$ | benzene sulfonic acid |
| Q-27 | N(CH$_2$CH$_2$CH$_3$)$_3$ | xylene sulfonic acid |
| Q-28 | N(CH$_2$CH$_2$CH$_3$)$_3$ | methane sulfonic acid |
| Q-29 | N(CH$_2$CH$_2$CH$_3$)$_3$ | trifluoromethyl sulfonic acid |
| Q-30 | N(CH$_2$CH$_2$CH$_3$)$_3$ | mesitylene sulfonic acid |
| Q-31 | N(CH$_2$CH$_2$CH$_2$CH$_3$)$_3$ | HF |
| Q-32 | N(CH$_2$CH$_2$CH$_2$CH$_3$)$_3$ | HCl |
| Q-33 | N(CH$_2$CH$_2$CH$_2$CH$_3$)$_3$ | HBr |
| Q-34 | N(CH$_2$CH$_2$CH$_2$CH$_3$)$_3$ | HI |

TABLE 1-continued

| No. | amine | Acid |
|---|---|---|
| Q-35 | N(CH₂CH₂CH₂CH₃)₃ | p-toluene sulfonic acid |
| Q-36 | N(CH₂CH₂CH₂CH₃)₃ | benzene sulfonic acid |
| Q-37 | N(CH₂CH₂CH₂CH₃)₃ | xylene sulfonic acid |
| Q-38 | N(CH₂CH₂CH₂CH₃)₃ | methane sulfonic acid |
| Q-39 | N(CH₂CH₂CH₂CH₃)₃ | trifluoromethyl sulfonic acid |
| Q-40 | N(CH₂CH₂CH₂CH₃)₃ | mesitylene sulfonic acid |
| Q-41 | N[CH(CH₃)₂]₃ | HF |
| Q-42 | N[CH(CH₃)₂]₃ | HCl |
| Q-43 | N[CH(CH₃)₂]₃ | HBr |
| Q-44 | N[CH(CH₃)₂]₃ | HI |
| Q-45 | N[CH(CH₃)₂]₃ | p-toluene sulfonic acid |
| Q-46 | N[CH(CH₃)₂]₃ | benzene sulfonic acid |
| Q-47 | N[CH(CH₃)₂]₃ | xylene sulfonic acid |
| Q-48 | N[CH(CH₃)₂]₃ | methane sulfonic acid |
| Q-49 | N[CH(CH₃)₂]₃ | trifluoromethyl sulfonic acid |
| Q-50 | N[CH(CH₃)₂]₃ | mesitylene sulfonic acid |
| Q-51 | N(CH₂CH₃)[(CH(CH₃)₂]₂ | HF |
| Q-52 | N(CH₂CH₃)[(CH(CH₃)₂]₂ | HCl |
| Q-53 | N(CH₂CH₃)[(CH(CH₃)₂]₂ | HBr |
| Q-54 | N(CH₂CH₃)[(CH(CH₃)₂]₂ | HI |
| Q-55 | N(CH₂CH₃)[(CH(CH₃)₂]₂ | p-toluene sulfonic acid |
| Q-56 | N(CH₂CH₃)[(CH(CH₃)₂]₂ | benzene sulfonic acid |
| Q-57 | N(CH₂CH₃)[(CH(CH₃)₂]₂ | xylene sulfonic acid |
| Q-58 | N(CH₂CH₃)[(CH(CH₃)₂]₂ | methane sulfonic acid |
| Q-59 | N(CH₂CH₃)[(CH(CH₃)₂]₂ | trifluoromethyl sulfonic acid |
| Q-60 | N(CH₂CH₃)[(CH(CH₃)₂]₂ | mesitylene sulfonic acid |
| Q-61 | DBU | HF |
| Q-62 | DBU | HCl |
| Q-63 | DBU | HBr |
| Q-64 | DBU | HI |
| Q-65 | DBU | p-toluene sulfonic acid |
| Q-66 | DBU | benzene sulfonic acid |
| Q-67 | DBU | xylene sulfonic acid |
| Q-68 | DBU | methane sulfonic acid |
| Q-69 | DBU | trifluoromethyl sulfonic acid |
| Q-70 | DBU | mesitylene sulfonic acid |
| Q-71 | DBN | HF |
| Q-72 | DBN | HCl |
| Q-73 | DBN | HBr |
| Q-74 | DBN | HI |
| Q-75 | DBN | p-toluene sulfonic acid |
| Q-76 | DBN | benzene sulfonic acid |
| Q-77 | DBN | xylene sulfonic acid |
| Q-78 | DBN | methane sulfonic acid |
| Q-79 | DBN | trifluoromethyl sulfonic acid |
| Q-80 | DBN | mesitylene sulfonic acid |
| Q-81 | methyl morpholine | HF |
| Q-82 | methyl morpholine | HCl |
| Q-83 | methyl morpholine | HBr |
| Q-84 | methyl morpholine | HI |
| Q-85 | methyl morpholine | p-toluene sulfonic acid |
| Q-86 | methyl morpholine | benzene sulfonic acid |
| Q-87 | methyl morpholine | xylene sulfonic acid |
| Q-88 | methyl morpholine | methane sulfonic acid |
| Q-89 | methyl morpholine | trifluoromethyl sulfonic acid |
| Q-90 | methyl morpholine | mesitylene sulfonic acid |
| Q-91 | ethyl morpholine | HF |
| Q-92 | ethyl morpholine | HCl |
| Q-93 | ethyl morpholine | HBr |
| Q-94 | ethyl morpholine | HI |
| Q-95 | ethyl morpholine | p-toluene sulfonic acid |
| Q-96 | ethyl morpholine | benzene sulfonic acid |
| Q-97 | ethyl morpholine | xylene sulfonic acid |
| Q-98 | ethyl morpholine | methane sulfonic acid |
| Q-99 | ethyl morpholine | trifluoromethyl sulfonic acid |
| Q-100 | ethyl morpholine | mesitylene sulfonic acid |
| Q-101 | N,N-dimethylaniline | HF |
| Q-102 | N,N-dimethylaniline | HCl |
| Q-103 | N,N-dimethylaniline | HBr |
| Q-104 | N,N-dimethylaniline | HI |
| Q-105 | N,N-dimethylaniline | p-toluene sulfonic acid |
| Q-106 | N,N-dimethylaniline | benzene sulfonic acid |
| Q-107 | N,N-dimethylaniline | xylene sulfonic acid |
| Q-108 | N,N-dimethylaniline | methane sulfonic acid |
| Q-109 | N,N-dimethylaniline | trifluoromethyl sulfonic acid |
| Q-110 | N,N-dimethylaniline | mesitylene sulfonic acid |
| Q-111 | methyl piperidine | HF |
| Q-112 | methyl piperidine | HCl |
| Q-113 | methyl piperidine | HBr |
| Q-114 | methyl piperidine | HI |
| Q-115 | methyl piperidine | p-toluene sulfonic acid |
| Q-116 | methyl piperidine | benzene sulfonic acid |
| Q-117 | methyl piperidine | xylene sulfonic acid |
| Q-118 | methyl piperidine | methane sulfonic acid |
| Q-119 | methyl piperidine | trifluoromethyl sulfonic acid |
| Q-120 | methyl piperidine | mesitylene sulfonic acid |
| Q-121 | methyl pyrrolidine | HF |
| Q-122 | methyl pyrrolidine | HCl |
| Q-123 | methyl pyrrolidine | HBr |
| Q-124 | methyl pyrrolidine | HI |
| Q-125 | methyl pyrrolidine | p-toluene sulfonic acid |
| Q-126 | methyl pyrrolidine | benzene sulfonic acid |
| Q-127 | methyl pyrrolidine | xylene sulfonic acid |
| Q-128 | methyl pyrrolidine | methane sulfonic acid |
| Q-129 | methyl pyrrolidine | trifluoromethyl sulfonic acid |
| Q-130 | methyl pyrrolidine | mesitylene sulfonic acid |
| Q-131 | methyl dibenzyl amine | HF |
| Q-132 | methyl dibenzyl amine | HCl |
| Q-133 | methyl dibenzyl amine | HBr |
| Q-134 | methyl dibenzyl amine | HI |
| Q-135 | methyl dibenzyl amine | p-toluene sulfonic acid |
| Q-136 | methyl dibenzyl amine | benzene sulfonic acid |
| Q-137 | methyl dibenzyl amine | xylene sulfonic acid |
| Q-138 | methyl dibenzyl amine | methane sulfonic acid |
| Q-139 | methyl dibenzyl amine | trifluoromethyl sulfonic acid |
| Q-140 | methyl dibenzyl amine | mesitylene sulfonic acid |
| Q-141 | pyridine | HF |
| Q-142 | pyridine | HCl |
| Q-143 | pyridine | HBr |
| Q-144 | pyridine | HI |
| Q-145 | pyridine | p-toluene sulfonic acid |
| Q-146 | pyridine | benzene sulfonic acid |
| Q-147 | pyridine | xylene sulfonic acid |
| Q-148 | pyridine | methane sulfonic acid |
| Q-149 | pyridine | trifluoromethyl sulfonic acid |
| Q-150 | pyridine | mesitylene sulfonic acid |
| Q-151 | DMAP | HF |
| Q-152 | DMAP | HCl |
| Q-153 | DMAP | HBr |
| Q-154 | DMAP | HI |
| Q-155 | DMAP | p-toluene sulfonic acid |
| Q-156 | DMAP | benzene sulfonic acid |
| Q-157 | DMAP | xylene sulfonic acid |
| Q-158 | DMAP | methane sulfonic acid |
| Q-159 | DMAP | trifluoromethyl sulfonic acid |
| Q-160 | DMAP | mesitylene sulfonic acid |
| Q-161 | collidine | HF |
| Q-162 | collidine | HCl |
| Q-163 | collidine | HBr |
| Q-164 | collidine | HI |
| Q-165 | collidine | p-toluene sulfonic acid |
| Q-166 | collidine | benzene sulfonic acid |
| Q-167 | collidine | xylene sulfonic acid |
| Q-168 | collidine | methane sulfonic acid |
| Q-169 | collidine | trifluoromethyl sulfonic acid |
| Q-170 | collidine | mesitylene sulfonic acid |
| Q-171 | lutidine | HF |
| Q-172 | lutidine | HCl |
| Q-173 | lutidine | HBr |
| Q-174 | lutidine | HI |
| Q-175 | lutidine | p-toluene sulfonic acid |
| Q-176 | lutidine | benzene sulfonic acid |
| Q-177 | lutidine | xylene sulfonic acid |
| Q-178 | lutidine | methane sulfonic acid |
| Q-179 | lutidine | trifluoromethyl sulfonic acid |
| Q-180 | lutidine | mesitylene sulfonic acid |
| Q-181 | pyrimidine | HF |
| Q-182 | pyrimidine | HCl |
| Q-183 | pyrimidine | HBr |
| Q-184 | pyrimidine | HI |
| Q-185 | pyrimidine | p-toluene sulfonic acid |
| Q-186 | pyrimidine | benzene sulfonic acid |
| Q-187 | pyrimidine | xylene sulfonic acid |
| Q-188 | pyrimidine | methane sulfonic acid |
| Q-189 | pyrimidine | trifluoromethyl sulfonic acid |
| Q-190 | pyrimidine | mesitylene sulfonic acid |

TABLE 1-continued

| No. | amine | Acid |
|---|---|---|
| Q-191 | pyrazine | HF |
| Q-192 | pyrazine | HCl |
| Q-193 | pyrazine | HBr |
| Q-194 | pyrazine | HI |
| Q-195 | pyrazine | p-toluene sulfonic acid |
| Q-196 | pyrazine | benzene sulfonic acid |
| Q-197 | pyrazine | xylene sulfonic acid |
| Q-198 | pyrazine | methane sulfonic acid |
| Q-199 | pyrazine | trifluoromethyl sulfonic acid |
| Q-200 | pyrazine | mesitylene sulfonic acid |
| Q-201 | piperazine | HF |
| Q-202 | piperazine | HCl |
| Q-203 | piperazine | HBr |
| Q-204 | piperazine | HI |
| Q-205 | piperazine | p-toluene sulfonic acid |
| Q-206 | piperazine | benzene sulfonic acid |
| Q-207 | piperazine | xylene sulfonic acid |
| Q-208 | piperazine | methane sulfonic acid |
| Q-209 | piperazine | trifluoromethyl sulfonic acid |
| Q-210 | piperazine | mesitylene sulfonic acid |
| Q-211 | $N(CH_3)_2CH_2CH_3$ | HF |
| Q-212 | $N(CH_3)_2CH_2CH_3$ | HCl |
| Q-213 | $N(CH_3)_2CH_2CH_3$ | HBr |
| Q-214 | $N(CH_3)_2CH_2CH_3$ | HI |
| Q-215 | $N(CH_3)_2CH_2CH_3$ | p-toluene sulfonic acid |
| Q-216 | $N(CH_3)_2CH_2CH_3$ | benzene sulfonic acid |
| Q-217 | $N(CH_3)_2CH_2CH_3$ | xylene sulfonic acid |
| Q-218 | $N(CH_3)_2CH_2CH_3$ | methane sulfonic acid |
| Q-219 | $N(CH_3)_2CH_2CH_3$ | trifluoromethyl sulfonic acid |
| Q-220 | $N(CH_3)_2CH_2CH_3$ | mesitylene sulfonic acid |
| Q-221 | $N(CH_3)_2CH_2CH_2CH_3$ | HF |
| Q-222 | $N(CH_3)_2CH_2CH_2CH_3$ | HCl |
| Q-223 | $N(CH_3)_2CH_2CH_2CH_3$ | HBr |
| Q-224 | $N(CH_3)_2CH_2CH_2CH_3$ | HI |
| Q-225 | $N(CH_3)_2CH_2CH_2CH_3$ | p-toluene sulfonic acid |
| Q-226 | $N(CH_3)_2CH_2CH_2CH_3$ | benzene sulfonic acid |
| Q-227 | $N(CH_3)_2CH_2CH_2CH_3$ | xylene sulfonic acid |
| Q-228 | $N(CH_3)_2CH_2CH_2CH_3$ | methane sulfonic acid |
| Q-229 | $N(CH_3)_2CH_2CH_2CH_3$ | trifluoromethyl sulfonic acid |
| Q-230 | $N(CH_3)_2CH_2CH_2CH_3$ | mesitylene sulfonic acid |
| Q-231 | $NCH_3(CH_2CH_3)_2$ | HF |
| Q-232 | $NCH_3(CH_2CH_3)_2$ | HCl |
| Q-233 | $NCH_3(CH_2CH_3)_2$ | HBr |
| Q-234 | $NCH_3(CH_2CH_3)_2$ | HI |
| Q-235 | $NCH_3(CH_2CH_3)_2$ | p-toluene sulfonic acid |
| Q-236 | $NCH_3(CH_2CH_3)_2$ | benzene sulfonic acid |
| Q-237 | $NCH_3(CH_2CH_3)_2$ | xylene sulfonic acid |
| Q-238 | $NCH_3(CH_2CH_3)_2$ | methane sulfonic acid |
| Q-239 | $NCH_3(CH_2CH_3)_2$ | trifluoromethyl sulfonic acid |
| Q-240 | $NCH_3(CH_2CH_3)_2$ | mesitylene sulfonic acid |

Amine acid complexes wherein the acid is hydrochloric acid or hydrobromic acid, especially hydrochloric acid, are preferred.

Also, amine acid complexes wherein the acid is p-toluene sulfonic acid, benzene sulfonic acid, or xylene sulfonic acid are preferred.

Amine acid complexes Q-2, Q-5, Q-12, Q-17, Q-22, Q-32, Q-42, Q-52, Q-142, Q-145, Q-147, Q-162, Q-165, Q-172, Q-175, Q-212, Q-215, Q-222, Q-225, Q-232, and Q-235 are preferred.

Even more preferred are amine acid complexes Q-2, Q-5, Q-6, Q-7, Q-12, Q-82, Q-85, Q-86, Q-87, Q-102, Q-105, Q-106, Q-107, Q-112, Q-115, Q-116, Q-117, Q-122, Q-125, Q-126, Q-127, Q-132, Q-135, Q-136, Q-137, Q-142, Q-145, Q-146, Q-147, Q-212, Q-215, Q-216, Q-217, Q-222, Q-225, Q-226, Q-227, Q-232, Q-235, Q-236, and Q-237.

Most preferred are amine acid complexes Q-2, Q-5, Q-6, Q-7, Q-12, Q-142, Q-145, Q-146, Q-147, Q-212, Q-215, Q-216, Q-217, Q-222, Q-225, Q-226, Q-227, Q-232, Q-235, Q-236, and Q-237.

With regard to their use in the inventive process, the combinations of sulfinylating agent and amine acid complex given in the tables below are especially preferred.

Table 2

Trifluoromethylsulfinate sodium salt is used as the sulfinylating agent, and the amine acid complex in each case is a row of table 1.

Table 3

Trifluoromethylsulfinate potassium salt is used as the sulfinylating agent, and the amine acid complex in each case is a row of table 1.

Table 4

Trifluoromethylsulfinic acid is used as the sulfinylating agent, and the amine acid complex in each case is a row of table 1.

Table 5

Trifluoromethylsulfinic acid anhydride is used as the sulfinylating agent, and the amine acid complex in each case is a row of table 1.

Table 6

A mixture of trifluoromethylsulfinate sodium and potassium salt in a mixing ratio of from 0.01:99.99 weight % to 50:50 weight % is used as the sulfinylating agent, and the amine acid complex in each case is a row of table 1.

Also, in a further embodiment of the present invention, a Lewis acid such as $AlCl_3$, $FeCl_3$, $CaCl_2$, $ZnCl_2$, $BF_3$, $TiCl_4$, or $ZrCl_4$ can be used in exchange for the protonic acids cited above.

It can be advantageous to add the amine acid complex in two portions, one portion for step 1 and one portion after the addition of the pyrazole of formula II.

It can be advantageous to use two different amine acid complexes during the course of the reaction. For example, the first amine acid complex can be added in step 1 in amounts of 0.2 to 1 molar equivalents relative to pyrazole II, catalyzing the activation of the sulfinylate with the halogenating agent. After addition of the pyrazole of formula II, in step 2, the Thia-Fries rearrangement, a second amine acid complex different from the first one is added, in amounts of 0.2 to 1 molar equivalents relative to pyrazole II.

Preferably, 1.4 to 2.2 molar equivalents, most preferably 1.5 to 1.8 molar equivalents, of the amine acid complex according to the present invention relative to 5-amino-1-[2,6-dichloro-4-(trifluoromethyl)phenyl]-1H-pyrazole-3-carbonitrile are used.

When the sulfinylating agent is trifluoromethylsulfinic acid or a mixture containing trifluoromethylsulfinic acid, the molar amount of amine acid complex which is molar equivalent to the molar amount of trifluoromethylsulfinic acid is preferably generated in situ by addition of amine, and the remaining molar amount necessary to obtain the required 1.4 to 2.2 molar equivalents is added as amine acid complex.

In a preferred embodiment, the amine acid complex is dried before its use until it is essentially water-free. "Water free" means that the content of water in the solid does not exceed 5 ppm to 100 ppm.

Further additives can advantageously be added to the reaction mixture, such as potassium fluoride, pentafluorophenol, dimethylformamide, or 2,4-dinitrophenol. These additives are preferably added to the reaction mixture or solution or suspension of starting materials, respectively, before or at the reaction start. Most preferably, the additives are added at a low temperature of 5° C. to 10° C.

In a preferred embodiment, 0.1 to 1.5 molar equivalents of potassium fluoride relative to 5-amino-1-[2,6-dichloro-4-(trifluoromethyl)phenyl]-1H-pyrazole-3-carbonitrile are added to the reaction mixture or solution or suspension of starting materials, respectively, at 5° C. to 10° C. at or before the reaction start.

Is advantageous to add pentafluorophenol, dimethylformamide, or 2,4-dinitrophenol in catalytic amounts or in 0.10 molar equivalents relative to 5-amino-1-[2,6-dichloro-4-(trifluoromethyl)phenyl]-1H-pyrazole-3-carbonitrile.

In a preferred embodiment, the additive is dried before its use until it is essentially water-free. "Water free" means that the content of water in the solid does not exceed 5 ppm to 100 ppm.

The reaction can be conducted in an inert organic solvent, preferably selected from aliphatic, alicyclic or aromatic, optionally halogenated hydrocarbons such as aromatic organic hydrocarbons, e.g. toluene, xylene, trifluoromethylbenzene, benzene, nitrobenzene, monochlorobenzene, dichlorobenzene, and ethylbenzene, preferably toluene and xylene, most preferably toluene; or aliphatic or alicyclic, optionally halogenated hydrocarbons such as hexane, cyclohexane, benzine, 1,2 dichloroethane, dichloromethane, trichloromethane (chloroform), tetrachlorocarbon, preferably 1,2 dichloroethane, dichloromethane, trichloromethane; and ethers, e.g. diethylether, dioxane, tetrahydrofuran, 2-methyl-tetrahydrofuran or ethylen glycol dimethyl- or diethylether; and ketons, e.g. acetone or butanon; and nitriles, e.g. acetonitrile or propionitrile; and amides, e.g. dimethylformamid, DMI (1,3-Dimethyl-2-Imidazolidinon), dimethyllacetamid, N-methylformanilid, N-methylpyrrolidon or hexamethylphosphoric acid triamide; and sulfoxides, e.g. dimethylsulfoxide.

In a preferred embodiment, solvents which are essentially water free are used. "Water free" means that the content of water in the solvent does not exceed 5 ppm to 100 ppm. The most preferred solvent is water free toluene.

The reaction is carried out under an inert gas atmosphere, such as under an argon or a nitrogen atmosphere.

In a preferred embodiment, a total of 3.0 to 8.0 molar equivalents, more preferably 4.0 to 7.5 molar equivalents, and most preferably 4.5 to 6.5 molar equivalents of the solvent relative to 5-amino-1-[2,6-dichloro-4-(trifluoromethyl)phenyl]-1H-pyrazole-3-carbonitrile are used. This relatively high concentration of starting materials maximizes the conversion to the sulfinamid intermediate.

In cases where the starting materials are dissolved and/or suspended, respectively, separately before their combination, about 25% to 40% of the solvent are employed for dissolving and/or suspending the 5-amino-1-[2,6-dichloro-4-(trifluoromethyl)phenyl]-1H-pyrazole-3-carbonitrile.

Generally, the sequence of addition of the starting materials 5-amino-1-[2,6-dichloro-4-(trifluoromethyl)phenyl]-1H-pyrazole-3-carbonitrile, amine acid complex, the sulfinylating agent and the chlorinating agent generally can be freely chosen.

Preferably, the respective starting materials are dissolved or suspended, respectively, in the reaction solvent before addition to the reaction mixture.

The halogenating agent is preferably not added to 5-amino-1-[2,6-dichloro-4-(trifluoromethyl)phenyl]-1H-pyrazole-3-carbonitrile in the absence of the amine acid complex or the sulfinylating agent in the reaction mixture. In a preferred embodiment, the halogenating agent is dissolved in the solvent and added to a reaction mixture containing 5-amino-1-[2,6-dichloro-4-(trifluoromethyl)phenyl]-1H-pyrazole-3-carbonitrile, amine acid complex and the sulfinylating agent, all dissolved or suspended, respectively, in the solvent.

In a preferred embodiment, 5-amino-1-[2,6-dichloro-4-(trifluoromethyl)phenyl]-1H-pyrazole-3-carbonitrile (II) is combined with a mixture containing the sulfinylating agent, the amine acid complex and the halogenating agent. In this case, it can be advantageous to include a first portion (equaling about 1 molar equivalent relative to compound II) of halogenating agent in the mixture containing the sulfinylating agent, the amine acid complex and the halogenating agent and then to add the second portion (equaling about 0.1 to 0.2 molar equivalents relative to compound II) after addition of the compound II and stirring for approximately 30 to 60 minutes and shortly before rising the temperature to 30 to 50° C.

When the sulfinylating agent is trifluoromethylsulfinic acid, it is preferred to simultaneously add the trifluoromethylsulfinic acid and the halogenating agent to a solution or suspension of the amine acid complex, followed by addition of a solution of 5-amino-1-[2,6-dichloro-4-(trifluoromethyl)phenyl]-1H-pyrazole-3-carbonitrile to the reaction mixture.

In another preferred embodiment, a dissolved or suspended mixture of the sulfinylating agent, the amine acid complex and the halogenating agent in the solvent (preferably toluene) is cooled to about 3° C. to 10° C., and a solution of 5-amino-1-[2,6-dichloro-4-(trifluoromethyl)phenyl]-1H-pyrazole-3-carbonitrile in the solvent (preferably toluene) which as been heated to about 90° C. to 110° C. is combined with the cooled mixture.

In a preferred embodiment, after combination of 5-amino-1-[2,6-dichloro-4-(trifluoromethyl)phenyl]-1H-pyrazole-3-carbonitrile, the sulfinylating agent, the amine acid complex, and the chlorinating agent, the temperature is raised to 30° C. to 55° C. within 5 to 60 minutes.

It is also preferred to hold the reaction temperature initially at −20° C. to 10° C. for 5 to 60 minutes, preferably 20 to 40 minutes, followed by rising the temperature to 30° C. to 55° C. at a rate of 5° C./min to 45° C./min. Preferably, in order to obtain high purity products, the reaction mixture is rised to a temperature not above 35° C. When the sulfinylating agent is or contains $CF_3S(O)OH$, the initial reaction temperature preferably is −20° C. to 5° C., in case of trifluoromethylsulfinate alkaline or alkaline earth metal salts, the initial reaction temperature preferably is −5° C. to 10° C.

The reaction time depends upon the reaction temperature, the temperature control during the process, and the different reagents and solvents. The skilled artisan will be able to determine the appropriate reaction time in order to achieve the desired yield and purity. Typically, the reaction time will be about 5 to 15 hours, preferably 10 to 15 hours.

In a further preferred embodiment, the reaction is carried out in a pressure vessel at a pressure of 1, 013 bar (1 atm) to about 4 bar.

After completion of the reaction, fipronil can be isolated by employing conventional methods such as quenching the reaction with hydrogen carbonates, such as $NaHCO_3$, carbonates such as $NaCO_3$, or hydroxides, such as NaOH, extracting fipronil with an unpolar organic solvent such as ethylacetate or methyl-tert.-butylether, washing the extract, e.g. with hydrogen carbonates such as $NaHCO_3$, concentrating the extract, e.g. in vacuo, crystallization of fipronil, and the like. The isolated fipronil can be purified by a technique such as chromatography, recrystallization and the like, if necessary.

The crystallization of the final product 5-amino-1-[2,6-dichloro-4-(trifluoromethyl)phenyl]-4-(trifluoromethylsulfinyl)-pyrazole-3-carbonitrile is typically conducted from a solution in a nonpolar, inert, preferably aromatic solvent with nonreactive substituents such as chloro, fluoro, cyano, nitro, $C_1$-$C_8$-alkyl, or $C_1$-$C_8$-haloalkyl, particularly from a solution in benzene, ethylbenzene, monochlorobenzene, monofluorobenzene, 1,2-dichlorobenzene, 1,3-dichlorobenzene, 1,4-dichlorobenzene, toluene, o-xylene, m-xylene, p-xylene, styrene, i-propyl benzene, n-propyl benzene, 2-chlorotoluene, 3-chlorotoluene, 4-chlorotoluene, tert.-butyl benzene, sec.-butyl benzene, iso-butyl benzene, n-butyl benzene, 1,3-diisopropylbenzene, 1,4-diisopropylbenzene, 2-nitrotoluene, 3-nitrotoluene, 4-nitrotoluene, nitrobenzene, benzonitrile, mesitylene, trifluoromethyl benzene, 1,2-dichloroethane, acetonitrile, dimethylsulfoxide, tetrahydrofuran, acetone, alcohols such as methanol, ethanol, n-propanol, isopropanol, n-butanol, isobutanol, 2-butanol, or tert-butanol, or mixtures thereof, preferably from a solution in monochlorobenzene, dichlorobenzene, ethylbenzene or toluene.

Preferably, the crystallization is done from monochlorobenzene.

Preferably, the crystallization is done from dichlorobenzene.

Preferably, the crystallization is done from ethylbenzene.

Preferably, the crystallization is done from toluene.

It can be advantageous to add about 1 to 30 percent of a polar solvent such as ketons, amides, alcohols, esters or ethers, preferably esters, ketons or ethers, such as acetone methyl ethyl ketone, pentan-2-one, diethylketone, 4-methyl-2-pentanone, 3-methyl-butan-2-one, tert-butyl-methyl-ketone, cyclohexanone, methylacetate, ethylacetate, isopropylacetate, N-butylacetate, isobutylacetate, diethylcarbonate, 2-butoxyethylacetate, dimethylformamide, dimethylacetamide, dimethylsulfoxide, nitromethane, nitroethane, water, ethanol, methanol, propan-1-ol, propan-2-ol, butan-1-ol, butan-2-ol, tert-butanol, 2-methyl-propan-1-ol, 2-methyl-propan-2-ol, pentan-3-ol, 2-methyl butan-1-ol, 3-methyl butan-1-ol, 1,2-ethanediol, 1,3-propandiol, 1,2-propandiol, cyclohexanol, dioxane, tetrahydrofurane, diethylether, methyl tert.-butyl ether, 2-methyl tetrahydrofuran, acetonitrile, propionitrile, or mixtures thereof.

In another embodiment, fipronil is crystallized from water, optionally with the addition of about 1 to 30 percent of a polar organic solvent.

Purification of the crude product can also be achieved via filtration over charcoal or silica or washing with water.

When obtained according to the inventive process, the obtained product fipronil in the crude reaction mixture before crystallization contains less than 3.0 weight %, calculated without solvent, of compound F, a typical, biologically active side product of fipronil syntheses.

Compound F

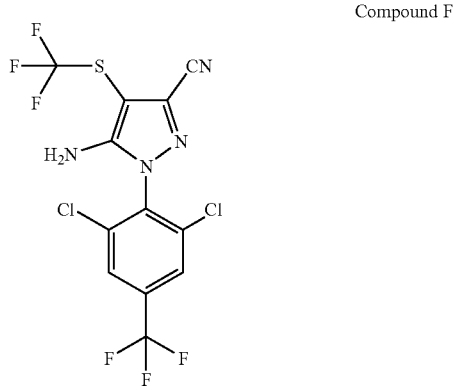

After purification of the crude product by suitable methods such as washing and (re-) crystallizing, fipronil obtained by the inventive process contains less than 1.0 weight % of compound F.

Besides, the obtained product fipronil contains less than 10 ppm of compound D which is a common side product of the currently large scale industrial process as described e.g. in WO 01/30760, even after purification. Fipronil when prepared by the inventive process in an inert atmosphere contains less than 200 ppm of compounds containing sulfur in its oxidation state (IV). It also is free of compound E which typically can appear as side product of the current industrial process.

Furthermore, the obtained product fipronil is also free of trifluoroacetic acid, which is a reagent used in the current industrial process.

Moreover, when a chlorinating agent is used as the halogenating agent, the obtained fipronil product is practically free of bromine, meaning that is does not contain more than 5 to 20 ppm of bromine.

EXAMPLES

HPLCs were taken on a Hewlett Packard HP 1200, Chemstation, equipped with a J'Sphere ODS-H80, 4 µm, 4.6×250 mm (YMC) column, eluent A: 90 wt.-% water+10 wt.-% acetonitrile, eluent B: 10 wt.-% water+90 wt.-% acetonitrile, flow: 0.85 ml/min, detection: 235 nm,

| | gradient: | | | | |
|---|---|---|---|---|---|
| time [min] | 0 | 2 | 17 | 25 | 35 |
| A [%] | 60 | 60 | 25 | 0 | 0 |
| B [%] | 40 | 40 | 75 | 100 | 100. |

Yields given below are in mol percent of the obtained purified crystalline product after work-up. Purity is given in weight percent of the obtained solid.

Example 1

Sulfinylation of 5-amino-1-[2,6-dichloro-4-(trifluoromethyl)phenyl]-1H-pyrazole-3-carbonitrile with triethylamine hydrochloride, sodium trifluoromethylsulfinate and thionylchloride, in 6.5 molar equivalents of toluene Within a 3-neck, 50 mL round bottom flask equipped with a magnetic stirrer bar and a thermometer were placed vacuum dried sodium trifluoromethylsulfinate (4.29 g, 27.5 mmol), vacuum dried triethylamine hydrochloride (5.16 g, 37.5 mmol), and 13 mL anhydrous toluene (6.5 molar equivalents relative to 5-amino-1-[2,6-dichloro-4-(trifluoromethyl)phenyl]-1H-pyrazole-3-carbonitrile) under an argon atmosphere. After cooling to 0° C. to 5° C. with an ice bath, thionylchloride (3.57 g, 30 mmol) was added slowly while keeping the reaction temperature below 5° C. After stirring for another 30 min, vacuum dried 5-amino-1-(2,6-dichloro-4-trifluoromethyl-phenyl)-1H-pyrazole-3-carbonitrile (8.03 g, 25 mmol, 99% purity) was added at 5° C., and the reaction mixture was heated to 50° C. within 5 min by a preheated water bath. The temperature of 50° C. was kept for another 6 hours before quenching the reaction with 50 mL of saturated NaHCO$_3$ solution.

The resulting suspension was diluted with 30 mL of ethylacetate. After phase separation the organic layer was washed once with saturated NaHCO$_3$ solution and concentrated under reduced pressure until dryness. The crude product was crystallized from refluxing toluene (100 g) affording the title compound as a white crystalline powder (8.06 g, 70% yield, 94% purity by quantitative HPLC). $^1$H-NMR (Bruker DRX-500, d$^6$-DMSO): δ [ppm]: 8.33 (s), 7.57 (s).

Example 2

Sulfinylation of 5-amino-1-[2,6-dichloro-4-(trifluoromethyl)phenyl]-1H-pyrazole-3-carbonitrile with triethylamine hydrochloride, potassium trifluoromethylsulfinate and thionylchloride Within a 3-neck, 50 mL round bottom flask equipped with a magnetic stirrer bar and a thermometer were placed vacuum dried potassium trifluoromethylsulfinate (4.73 g, 27.5 mmol), vacuum dried triethylamine hydrochloride (5.16 g, 37.5 mmol), thionylchloride (3.57 g, 30 mmol), and 15 mL anhydrous toluene under an argon atmosphere. The reaction is further conducted as described above for example 1.

The crude product was crystallized from refluxing chlorobenzene (100 g) affording the title compound as a white crystalline powder (7.44 g, 66% yield, 96% purity by quantitative HPLC). $^1$H-NMR (Bruker DRX-500, d$^6$-DMSO): δ [ppm]: 8.33 (s), 7.57 (s).

Example 3

Sulfinylation of 5-amino-1-[2,6-dichloro-4-(trifluoromethyl)phenyl]-1H-pyrazole-3-carbonitrile via addition of a mixture of sodium trifluoromethylsulfinate, triethylamine hydrochloride and thionylchloride to 5-amino-1-[2,6-dichloro-4-(trifluoromethyl)phenyl]-1H-pyrazole-3-carbonitrile Within a 3-neck, 50 mL round bottom flask equipped with a magnetic stirrer bar and a thermometer were placed vacuum dried sodium trifluoromethylsulfinate (4.29 g, 27.5 mmol), vacuum dried triethylamine hydrochloride (5.16 g, 37.5 mmol), and 10 g anhydrous toluene under an argon atmosphere. After cooling to 0-5° C. with an ice bath thionylchloride (3.57 g, 30 mmol) was added while keeping the reaction temperature below 5° C. After stirring for another 30 min the cooled sulfinic acid solution was added at once to a stirred suspension of vacuum dried 5-amino-1-(2,6-dichloro-4-trifluoromethyl-phenyl)-1H-pyrazole-3-carbonitrile (8.03 g, 25 mmol, 99% purity) in 5 g toluene with a temperature of 50° C. The temperature of 50° C. was kept for another 5 hours before quenching the reaction with 50 mL of saturated NaHCO$_3$ solution. The resulting suspension was diluted with 30 mL of ethylacetate. After phase separation the organic layer was washed once with saturated NaHCO$_3$ solution and concentrated under reduced pressure until dryness. The crude product was crystallized from refluxing toluene (100 g) affording the title compound as a white crystalline powder (7.25 g, 63% yield, 94% purity by quantitative HPLC). $^1$H-NMR (Bruker DRX-500, d$^6$-DMSO): δ [ppm]: 8.33 (s), 7.57 (s).

Example 4

Sulfinylation of 5-amino-1-[2,6-dichloro-4-(trifluoromethyl)phenyl]-1H-pyrazole-3-carbonitrile with triethylamine hydrochloride, trifluoromethylsulfinic acid and thionylchloride Within a 3-neck, 50 mL round bottom flask equipped with a magnetic stirrer bar and a thermometer were placed trifluoromethylsulfinic acid (3.69 g, 27.5 mmol), anhydrous triethylamine (2.78 g, 27.5 mmol), and 10 g anhydrous toluene under an argon atmosphere. After cooling to 0-5° C. with an ice bath thionylchloride (3.57 g, 30 mmol) was added while keeping the reaction temperature below 5° C. After stirring for another 30 min, the cooled sulfinic acid solution was added at once to a stirred suspension of vacuum dried 5-amino-1-(2,6-dichloro-4-trifluoromethyl-phenyl)-1H-pyrazole-3-carbonitrile (8.03 g, 25 mmol, 99% purity) and vacuum dried triethylamine hydrochloride (1.38 g, 10.0 mmol) in 5 g anhydrous toluene in a second 50 mL round bottom flask equipped with a magnetic stirrer bar and a thermometer having a temperature of 50° C. inside. The temperature of 50° C. was kept for another 6 hours before quenching the reaction with 50 mL of saturated NaHCO$_3$ solution.

The resulting suspension was diluted with 30 mL of ethylacetate. After phase separation the organic layer was washed once with saturated NaHCO$_3$ solution and concentrated under reduced pressure until dryness. The crude product was crystallized from refluxing toluene (100 g) affording the title compound as a white crystalline powder. $^1$H-NMR (Bruker DRX-500, d$^6$-DMSO): δ [ppm]: 8.33 (s), 7.57 (s).

Example 5

Sulfinylation of 5-amino-1-[2,6-dichloro-4-(trifluoromethyl)phenyl]-1H-pyrazole-3-carbonitrile with triethylamine hydrochloride, sodium trifluoromethylsulfinate and thionylchloride under addition of potassium fluoride An oven dried 100 mL 3 neck round bottom flask equipped with a magnetic stir bar, thermocouple, condenser, N$_2$ inlet, and rubber septum, was charged with vacuum dried potassium fluoride (1.53 g, 26.1 mmol), anhydrous toluene (20.1 g), vacuum dried sodium trifluoromethylsulfinate (4.53 g, 29.0 mmol), and thionylchloride (3.76 g, 31.6 mmol) under nitrogen. The solution was cooled to 0° C. and triethylamine hydrochloride (5.44 g, 39.5 mmol) was added slowly, controlling the temperature to less than 10° C. Vacuum dried 5-amino-1-(2,6-dichloro-4-trifluoromethyl-phenyl)-1H-pyrazole-3-carbonitrile (8.48 g, 26.1 mmol, 99% pure) was added at 0° C. The solution was then quickly warmed to 50° C., in less then 5 minutes, using a hot water bath. The reaction was allowed to stir for 5 hrs at 50° C. before quenching with 50 ml of saturated aqueous NaHCO$_3$. The resulting suspension was diluted with 30 mL of ethylacetate and then allowed to phase separate. The aqueous phase was extracted with 30 mL ethyl acetate and the combined organic phases were washed with 30 ml of saturated aqueous NaCO$_3$. The organic phase was concentrated under reduced pressure until dryness, affording the crude title compound (11.6 g, 67% yield, 68.5% purity). $^1$H-NMR (Bruker DRX-500, d$^6$-DMSO): δ [ppm]: 8.33 (s), 7.57 (s).

Example 6

Sulfinylation of 5-amino-1-[2,6-dichloro-4-(trifluoromethyl)phenyl]-1H-pyrazole-3-carbonitrile with triethylamine hydrochloride, sodium trifluoromethylsulfinate and phosphoroxychloride Within a 3-neck, 50 mL round bottom flask equipped with a magnetic stirrer bar and a thermometer were placed sodium trifluoromethylsulfinate (8.84 g, 55.0 mmol) and 40 mL dried toluene (6.8 molar equivalents relative to 5-amino-1-[2,6-dichloro-4-(trifluoromethyl)phenyl]-1H-pyrazole-3-carbonitrile) under a nitrogen atmosphere. After cooling to 0° C. to 5° C. with an ice bath, phosphoroxychloride (9.20 g, 60.0 mmol) was added slowly while keeping the reaction temperature below 5° C. After complete addition of phosphoroxychloride, triethylamine hydrochloride (10.32 g, 75.0 mmol) was added at 5° C. After stirring for another 30 min, vacuum dried 5-amino-1-(2,6-dichloro-4-trifluoromethyl-phenyl)-1H-pyrazole-3-carbonitrile (16.06 g, 50 mmol, 99% purity) was added at 5° C., and the reaction mixture was heated to 50° C. within 5 min by a preheated water bath. The temperature of 50° C. was kept for another 6 hours before quenching the reaction with 100 g of 10% NaHCO₃ solution. The resulting suspension was diluted with 100 mL of ethylacetate. After phase separation, the organic layer was analyzed by quantitative HPLC (57.3% yield).

Example 7

Sulfinylation of 5-amino-1-[2,6-dichloro-4-(trifluoromethyl)phenyl]-1H-pyrazole-3-carbonitrile with pyridine tosylate, sodium trifluoromethylsulfinate and thionylchloride, in 6.5 molar equivalents of toluene The preparation procedure was conducted as described above for example 1. The crude product was crystallized from refluxing toluene (100 g) affording the title compound as a white crystalline powder (75% yield, 94% purity by quantitative HPLC).

Example 8

Sulfinylation of 5-amino-1-[2,6-dichloro-4-(trifluoromethyl)phenyl]-1H-pyrazole-3-carbonitrile with trimethylamine hydrochloride, sodium trifluoromethylsulfinate and thionylchloride, in 6.5 molar equivalents of toluene The preparation procedure was conducted as described above for example 1. The crude product was crystallized from refluxing toluene (100 g) affording the title compound as a white crystalline powder (71% yield, 97% purity by quantitative HPLC).

Example 9

Sulfinylation of 5-amino-1-[2,6-dichloro-4-(trifluoromethyl)phenyl]-1H-pyrazole-3-carbonitrile with pyridine hydrochloride, sodium trifluoromethylsulfinate and thionylchloride, in 6.5 molar equivalents of toluene The preparation procedure was conducted as described above for example 1. The crude product was crystallized from refluxing toluene (100 g) affording the title compound as a white crystalline powder (67% yield, 95% purity by quantitative HPLC).

Example 10

Sulfinylation of 5-amino-1-[2,6-dichloro-4-(trifluoromethyl)phenyl]-1H-pyrazole-3-carbonitrile with triethylamine hydrochloride, potassium trifluoromethylsulfinate and thionylchloride, in 4.5 molar equivalents of toluene Within a 3-neck, 50 mL round bottom flask equipped with a magnetic stirrer bar and a thermometer were placed vacuum dried potassium trifluoromethylsulfinate (5.16 g, 30 mmol), vacuum dried triethylamine hydrochloride (5.16 g, 37.5 mmol), and 10.4 g anhydrous toluene (4.5 molar equivalents relative to 5-amino-1-[2,6-dichloro-4-(trifluoromethyl)phenyl]-1H-pyrazole-3-carbonitrile) under an argon atmosphere. After cooling to 0° C. to 5° C. with external cooling, thionylchloride (3.57 g, 30 mmol) was added within 15 min while keeping the reaction temperature below 5° C. After stirring for another 30 min, vacuum dried 5-amino-1-(2,6-dichloro-4-trifluoromethyl-phenyl)-1H-pyrazole-3-carbonitrile (8.03 g, 25 mmol, 99% purity) was added at 5° C., and the reaction mixture was kept at 5° C. for 60 min and then heated to 35° C. within 45 min. The temperature of 35° C. was kept for 3 hours before adding 4.6 g of toluene. After another 7 hours at 35° C. the reaction was quenched with 20 g of sodium hydroxide solution (10 wt. %).

The resulting suspension was diluted with 30 mL of ethylacetate. After phase separation the organic layer was washed once with sodium hydroxide solution (10 wt. %). After phase separation, the organic layer was analyzed by quantitative HPLC (80.4% yield). The crude product was crystallized from a mixture of ethylacetate and toluene affording the title compound as a white crystalline powder (7.98 g, 73% yield, 98% purity by quantitative HPLC).

Example 11

Sulfinylation of 5-amino-1-[2,6-dichloro-4-(trifluoromethyl)phenyl]-1H-pyrazole-3-carbonitrile with thionylchloride, triethylamine hydrochloride and dosage of potassium trifluoromethylsulfinate Within a 750 mL reactor with a mechanical stirrer and a thermometer were placed vacuum dried triethylamine hydrochloride (51.1 g, 368 mmol), 147 g anhydrous toluene (6.5 molar equivalents relative to 5-amino-1-[2,6-dichloro-4-(trifluoromethyl)phenyl]-1H-pyrazole-3-carbonitrile), and thionylchloride (35.7 g, 294 mmol) under an argon atmosphere. After cooling to 0° C. to 5° C. with external cooling, vacuum dried potassium trifluoromethylsulfinate (50.4 g, 296 mmol) was added in three equal portions every 10 min while keeping the reaction temperature below 5° C. After stirring for another 30 min, vacuum dried 5-amino-1-(2,6-dichloro-4-trifluoromethyl-phenyl)-1H-pyrazole-3-carbonitrile (79.5 g, 245 mmol, 99% purity) was added at 5° C., and the reaction mixture was kept at 5° C. for 60 min and then heated to 35° C. within 45 min. The temperature of 35° C. was kept for another 10 hours before quenching the reaction with 200 g of sodium hydroxide solution (10 wt. %).

The resulting suspension was diluted with 176 mL of ethylacetate. After phase separation the organic layer was washed once with sodium hydroxide solution (10 wt. %). After phase separation, the organic layer was analyzed by quantitative HPLC (79% yield). The content of compound F was below 2.9 weight percent in the crude mixture (without solvent). The product was crystallized from a mixture of ethylacetate and toluene affording the title compound as a white crystalline powder (77.1 g, 75% yield, 98% purity by quantitative HPLC).

Example 12

Sulfinylation of 5-amino-1-[2,6-dichloro-4-(trifluoromethyl)phenyl]-1H-pyrazole-3-carbonitrile with trimethylamine tosylate, sodium trifluoromethylsulfinate and thionylchloride, in 6.5 molar equivalents of toluene The preparation procedure was conducted as described above for example 1. The crude product was crystallized from refluxing toluene (100 g) affording the title compound as a white crystalline powder (76% yield, 96% purity by quantitative HPLC).

Example 13

Sulfinylation of 5-amino-1-[2,6-dichloro-4-(trifluoromethyl)phenyl]-1H-pyrazole-3-carbonitrile with pyridine hydrochloride, sodium trifluoromethylsulfinate and thionylchloride, in 6.5 molar equivalents of toluene The preparation procedure was conducted as described above for example 1. The crude product was crystallized from refluxing toluene (100 g) affording the title compound as a white crystalline powder (67% yield, 95% purity by quantitative HPLC).

Example 14

Sulfinylation of 5-amino-1-[2,6-dichloro-4-(trifluoromethyl)phenyl]-1H-pyrazole-3-carbonitrile with trimethylamine tosylate, sodium trifluoromethylsulfinate and thionylchloride, in 6.5 molar equivalents of toluene The preparation procedure was conducted as described above for example 11. The crude product was crystallized from refluxing toluene (100 g) affording the title compound as a white crystalline powder (73% yield, 98% purity by quantitative HPLC).

Example 15

Sulfinylation of 5-amino-1-[2,6-dichloro-4-(trifluoromethyl)phenyl]-1H-pyrazole-3-carbonitrile with triethylamine hydrochloride, sodium trifluoromethylsulfinate and thionylchloride, in 6.5 molar equivalents of toluene The preparation procedure was conducted as described above for example 11. The crude product was crystallized from refluxing toluene (100 g) affording the title compound as a white crystalline powder (75% yield, 98% purity by quantitative HPLC).

Example 16

Sulfinylation of 5-amino-1-[2,6-dichloro-4-(trifluoromethyl)phenyl]-1H-pyrazole-3-carbonitrile with pyridine tosylate, sodium trifluoromethylsulfinate and thionylchloride, in 6.5 molar equivalents of toluene The preparation procedure was conducted as described above for example 11. The crude product was crystallized from refluxing toluene (100 g) affording the title compound as a white crystalline powder (72% yield, 98% purity by quantitative HPLC).

Example 17

Sulfinylation of 5-amino-1-[2,6-dichloro-4-(trifluoromethyl)phenyl]-1H-pyrazole-3-carbonitrile with triethylamine tosylate, sodium trifluoromethylsulfinate and thionylchloride, in 6.5 molar equivalents of toluene The preparation procedure was conducted as described above for example 1. The crude product was crystallized from refluxing toluene (100 g) affording the title compound as a white crystalline powder (44% yield, 76% purity by quantitative HPLC). No formation of insoluble material (as with diethylamine tosylate as the amine acid complex, compare example C4 of Table 3) was observed.

COMPARATIVE EXAMPLES

In order to demonstrate the advantages of the inventive process, the following examples are conducted employing the preparation procedure given above for example 1.

TABLE 2

| No. | Sulfinylating agent | Amine acide complex | Chlorinating agent |
|---|---|---|---|
| C1 | $CF_3S(O)ONa$ | dimethylamine hydrochloride | $SOCl_2$ |
| C2 | $CF_3S(O)ONa$ | diethylamine hydrochloride | $SOCl_2$ |
| C3 | $CF_3S(O)ONa$ | diethylamine tosylate | $SOCl_2$ |

In these experiments, it is demonstrated that the inventive process gives higher yields and/or higher purities as compared to the sulfinylation processes described in the prior art. The results are summarized in Table 3 which follows.

TABLE 3

| Example no. | Sulfinylating Agent | Amine Acid Complex | Chlorinating Agent | Yield Crystalline Fipronil [mol %] | Purity of Fipronil [weight %] | Comments |
|---|---|---|---|---|---|---|
| Exp. 8 | $CF_3S(O)ONa$ | trimethylamine hydrochloride | $SOCl_2$ | 71 | 97 | |
| C1 | $CF_3S(O)ONa$ | dimethylamine hydrochloride | $SOCl_2$ | 57 | 84 | Disadvantageously, an insoluble material was formed that remained throughout the work-up and recrystallization |
| Exp. 1 | $CF_3S(O)ONa$ | triethylamine hydrochloride | $SOCl_2$ | 70 | 94 | |
| C2 | $CF_3S(O)ONa$ | diethylamine hydrochloride | $SOCl_2$ | 55 | 84 | Disadvantageously, an insoluble material was formed that remained throughout the work-up and recrystallization |
| Exp. 12 | $CF_3S(O)ONa$ | trimethylamine tosylate | $SOCl_2$ | 76 | 96 | |
| C3 | $CF_3S(O)ONa$ | dimethylamine tosylate | $SOCl_2$ | 73 | 97 | |
| Exp. 17 | $CF_3S(O)ONa$ | triethylamine tosylate | $SOCl_2$ | 44 | 76 | |

TABLE 3-continued

| Example no. | Sulfinylating Agent | Amine Acid Complex | Chlorinating Agent | Yield Crystalline Fipronil [mol %] | Purity of Fipronil [weight %] | Comments |
| --- | --- | --- | --- | --- | --- | --- |
| C4 | $CF_3S(O)ONa$ | diethylamine tosylate | $SOCl_2$ | 65 | 95 | Disadvantageously, an insoluble material was formed that remained throughout the work-up and recrystallization |

Further comparative experiments are conducted employing the following preparation procedure:

To a 750 ml reactor with a mechanical stirrer and a thermometer containing the amine acid complex (1.5 eq.), 147 g anhydrous toluene (6.5 eq.), and 44.8 g $CF_3SOCl$ (1.2 eq.) under an argon atmosphere at 0° C. was added vacuum dried 5-amino-1-(2,6-dichloro-4-trifluoromethyl-phenyl)-1H-pyrazole-3-carbonitrile (1 eq., 79.5 g, 245 mmol, 99% purity). The reaction mixture was kept at 5° C. for 60 min and then heated to 35° C. within 45 min. The temperature of 35° C. was kept for another 10 hours before quenching the reaction with 200 g of sodium hydroxide solution (10 wt. %).

The resulting suspension was diluted with 176 ml of ethylacetate. After phase separation the organic layer was washed once with sodium hydroxide solution (10 wt. %). After phase separation, the organic layer was analyzed by quantitative HPLC. The product was crystallized from a mixture of ethylacetate and toluene affording the title compound as a white crystalline powder.

| No. | Sulfinylating agent | Amine acide complex | Chlorinating agent |
| --- | --- | --- | --- |
| Ca | $CF_3S(O)Cl$ | pyridine hydrochloride | — |
| Cb | $CF_3S(O)Cl$ | trimethylamine hydrochloride | — |

These experiments Ca and Cb where compared to examples 18 and 19, which were conducted as described above for example 11, employing potassium trifluoromethylsulfinate/pyridine hydrochloride/$SOCl_2$ and potassium trifluoromethylsulfinate/trimethylamine hydrochloride/$SOCl_2$ as reagents.

In these experiments, it is demonstrated that the inventive process gives higher yields and/or higher purities as compared to the sulfinylation processes described in the prior art.

The invention claimed is:

1. A process for preparing fipronil consisting essentially of sulfinylating 5-amino-1-[2,6-dichloro-4-(trifluoromethyl)phenyl]-1H-pyrazole-3-carbonitrile (II) by reacting II with
   a sulfinylating agent selected from the group consisting of trifluoromethylsulfinic acid, alkaline or alkaline earth metal salt and mixtures of the acid and the salt(s), in the presence of at least one amine acid complex wherein the amine(s) are selected from $sp^3$-hybridized tertiary amines and the acid(s) is hydrochloric acid, and
   thionylchloride.

2. The process of claim 1, wherein said amine of the amine acid complex is selected from the group consisting of trimethylamine, triethylamine, dimethyl ethyl amine, and dimethyl n-propyl amine.

3. The process of claim 2, wherein said amine is trimethylamine, or triethylamine.

4. The process of claim 1, wherein at least one of the substituents on the $sp^3$-hybridized nitrogen of the amine is a methyl group.

5. The process of claim 1, wherein said sulfinylating agent is selected from the group consisting of trifluoromethylsulfinic acid, trifluoromethylsulfinate sodium salt, and trifluoromethylsulfinate potassium salt, and mixtures of these.

6. The process of claim 1, wherein said reaction is conducted in an organic solvent selected from the group consisting of toluene, benzene, xylene, trifluoromethylbenzene, monochlorobenzene, dichlorobenzene, and ethylbenzene.

7. The process of claim 1, wherein said reacting comprises combining 5-amino-1-[2,6-dichloro-4-(trifluoromethyl)phenyl]-1H-pyrazole-3-carbonitrile with a reaction mixture of said sulfinylating agent, said amine acid complex and said halogenating agent.

8. The process of claim 1, wherein 1.4 to 2.2 molar equivalents of said amine acid complex relative to 5-amino-1-[2,6-dichloro-4-(trifluoromethyl)phenyl]-1H-pyrazole-3-carbonitrile are present.

9. The process of claim 1, wherein 1.15 to 1.35 molar equivalents of said halogenating agent relative to 5-amino-1-[2,6-dichloro-4-(trifluoromethyl)phenyl]-1H-pyrazole-3-carbonitrile are present.

10. The process of claim 1, wherein 1.0 to 1.35 molar equivalents of said sulfinylating agent relative to 5-amino-1-[2,6-dichloro-4-(trifluoromethyl)phenyl]-1H-pyrazole-3-carbonitrile are present.

11. The process of claim 1, wherein said reacting comprises, after combining 5-amino-1-[2,6-dichloro-4-(trifluoromethyl)phenyl]-1H-pyrazole-3-carbonitrile, said sulfinylating agent, said amine acid complex, and said halogenating agent, the temperature is raised to 30° C. to 55° C., within 5 to 60 minutes.

12. The process of claim 1, wherein said reacting comprises, after combining 5-amino-1-[2,6-dichloro-4-(trifluoromethyl)phenyl]-1H-pyrazole-3-carbonitrile, said sulfinylating agent, said amine acid complex, and said halogenating agent, the temperature is raised to 30° C. to 39° C., within 5 to 60 minutes.

13. The process of claim 1, further comprising crystallizing 5-amino-1-[2,6-dichloro-4-(trifluoromethyl)phenyl]-4-(trifluoromethylsulfinyl)-pyrazole-3-carbonitrile from a solution of monochlorobenzene, dichlorobenzene, ethylbenzene or toluene.

14. The process of claim 1, further comprising admixing 5-amino-1-[2,6-dichloro-4-(trifluoromethyl)phenyl]-4-(trifluoromethylsulfinyl)-pyrazole-3-carbonitrile with a pesticidally acceptable carrier.

15. The process of claim 1, further comprising admixing 5-amino-1-[2,6-dichloro-4-(trifluoromethyl)phenyl]-4-(trifluoromethylsulfinyl)-pyrazole-3-carbonitrile with a veterinarily acceptable carrier.

16. The process of claim 1, wherein the process yields less than 20 ppm of bromine.

17. The process of claim 1, wherein the process yields less than 10 ppm of the compound D
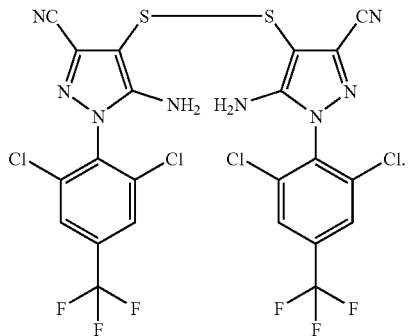
Compound D
18. The process of claim 1, wherein the process yields less than 3% of the compound F:
Compound F
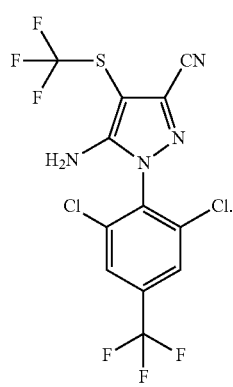
* * * * *